(12) United States Patent
Beyrard et al.

(10) Patent No.: US 8,848,859 B2
(45) Date of Patent: Sep. 30, 2014

(54) X-RAY OR INFRARED IMAGING DEVICE COMPRISING A DOSE LIMITER, WITH CONTROLLED TRANSLATION SPEED

(75) Inventors: Norbert Beyrard, Divonne-les-Bains (FR); Franck Hereson, Fontaine (FR)

(73) Assignee: Norbert Beyrard, Divonne-les-Bains (FR)

( * ) Notice: Subject to any disclaimer, the term of this patent is extended or adjusted under 35 U.S.C. 154(b) by 592 days.

(21) Appl. No.: 13/139,035

(22) PCT Filed: Dec. 10, 2009

(86) PCT No.: PCT/EP2009/066818
§ 371 (c)(1),
(2), (4) Date: Jun. 10, 2011

(87) PCT Pub. No.: WO2010/081598
PCT Pub. Date: Jul. 22, 2010

(65) Prior Publication Data
US 2011/0243297 A1    Oct. 6, 2011

(30) Foreign Application Priority Data

Jan. 13, 2009 (FR) .................................... 09 00118
Apr. 27, 2009 (FR) .................................... 09 02018

(51) Int. Cl.
| | |
|---|---|
| *A61B 6/03* | (2006.01) |
| *G21K 1/02* | (2006.01) |
| *G21K 1/04* | (2006.01) |
| *A61B 6/06* | (2006.01) |
| *A61B 6/00* | (2006.01) |

(52) U.S. Cl.
CPC ............... *G21K 1/025* (2013.01); *A61B 6/4488* (2013.01); *G21K 1/046* (2013.01); *A61B 6/587* (2013.01); *A61B 6/032* (2013.01); *A61B 6/542* (2013.01); *A61B 6/06* (2013.01)
USPC .............................................................. 378/4

(58) Field of Classification Search
CPC .................................................... A61B 6/0306
USPC ...................................................... 378/4, 19, 62
See application file for complete search history.

(56) References Cited

U.S. PATENT DOCUMENTS

| | | | |
|---|---|---|---|
| 5,857,008 A | 1/1999 | Reinhold | |
| 6,320,929 B1 * | 11/2001 | Von Der Haar | ................... 378/4 |
| 6,429,572 B1 | 8/2002 | Beyrard | |
| 2003/0063703 A1 | 4/2003 | Moore | |
| 2008/0118023 A1 | 5/2008 | Besson | |

FOREIGN PATENT DOCUMENTS

| | | |
|---|---|---|
| DE | 102006005619 | 8/2006 |
| EP | 1058322 | 12/2000 |

(Continued)

*Primary Examiner* — Irakli Kiknadze
(74) *Attorney, Agent, or Firm* — Sturm & Fix LLP

(57) ABSTRACT

An X-ray or infrared imagery apparatus that performs a large sweep while reducing the irradiation or illumination dose. It comprises a support, an X-ray or light ray source that emits a beam through a slit of a dose limiter which is driven in translation, a detector irradiated or illuminated by the beam in order to detect an intensity attenuated along the X-ray or light ray propagation path through the body, an analog-to-digital converter to convert the detected intensities into data in order to determine an attenuation of the X-rays or light rays by the body, and a programmed computer to process the data in order to obtain an image representing the attenuation of the X-rays or light rays. The dose limiter either is driven in translation at a speed proportional to the detector or driven in translation at the same speed than the detector in front of a reflector.

17 Claims, 9 Drawing Sheets

(56) References Cited

FOREIGN PATENT DOCUMENTS

| | | |
|---|---|---|
| FR | 2844916 | 3/2004 |
| FR | 2871911 | 12/2005 |
| FR | 2888374 | 1/2007 |
| WO | 2006003312 | 1/2006 |
| WO | 2007006560 | 1/2007 |

* cited by examiner

X-RAY OR INFRARED IMAGING DEVICE COMPRISING A DOSE LIMITER, WITH CONTROLLED TRANSLATION SPEED

BACKGROUND OF THE INVENTION

1. Field of the Invention

The invention refers to an X-ray or infrared imagery apparatus, for radiography or scanning, comprising particularly:
- a support for receiving a body to be examined,
- a X-ray or light ray source provided with a focus for emitting a beam passing through a slit of a dose limiter driven in translation to sweep the body,
- a detector driven in translation to be irradiated or illuminated by the beam sweeping the body in order to detect an intensity attenuated along the X-ray or light ray propagation path through the body,
- an analog-to-digital converter to convert the detected intensities into data in order to determine an attenuation of the X-rays or light rays by the body, and
- a programmed computer to process the data resulting from the conversion of the detected intensities in order to obtain an image representing the attenuation of the X-rays or light rays by the examined body.

2. Description of the Related Art

An apparatus of this type is especially known from French patent application FR A-2 888 374 filed by the applicant. The detector is shaped with a detection rod and the dose limiter is driven in translation at the same speed and in the same direction as the detector to reduce the body exposure to the just necessary irradiation or illumination of the rod. The synchronous move of the dose limiter and the detector with respect to the fixed source tends to misalign these three elements. The misalignment effect is however kept at an acceptable level if the rays are emitted by the source with a low angle of divergence compared to the axial direction of the beam, thus enabling the source to be maintained in fixed position for a typical width sweeping. For a greater sweeping, for example twice the typical width, the effect of misalignment requires to successively carry out two sweepings starting from two fixed positions of the source.

SUMMARY OF THE INVENTION

The purpose of the invention is to modify an apparatus of the type indicated below to increase the sweeping width for a given position of the source in order to obtain radiography or scanning images of large width, typically about 50 cm, while reducing the X-ray or light ray exposure to the just necessary irradiation or the illumination of the detector.

For this purpose, the object of the invention is an apparatus in conformity with the apparatus aforementioned, wherein the dose limiter is driven in translation at a speed proportional to the detector, controlled by the ratio of the distances between, on the one hand, the focus and the detector and, on the other hand, the focus and the dose limiter.

By such a dose limiter and detector speed control, alignment between focus, dose limiter slit and detector is constant. This enables a body sweep over a substantial width without moving the source, by using not only the slightly diverging rays but also the more diverging rays, within a cone of divergence chosen with respect to the distances between, on the one hand, the focus and the dose limiter and, on the other hand, the focus and the detector. The alignment between focus, dose limiter slit and detector enables to sweep the body while reducing the dose to the just necessary irradiation or the illumination of the detector.

According to a particular embodiment of the invention, the X-ray or light ray beam is a secondary beam, resulting from a virtual focus formed by a primary beam emitted by an actual focus supplied by the source and reflected by a double reflection reflector laid out between the source and the dose limiter. The dose limiter is moved in translation in the same direction as the detector, when it is laid out between the virtual focus and the body. It is moved in the direction opposed to the detector when it is laid out between the double reflexion reflector and the virtual focus.

The invention embraces an apparatus in conformity with the apparatus aforementioned, wherein the dose limiter is driven in translation at the same speed than the detector in front of a reflector, irradiating or illuminating the body by means of reflective rays emitted by the source along parallel webs. This enables a sweep of the body over a substantial width corresponding to an output section of the reflector without moving the source but using the reflected rays along the parallel webs. The control of the synchronous move of the dose limiter slit and the detector enables to reduce the dose to the just necessary irradiation or illumination of the detector.

The invention advantageously enables to obtain large width and high definition images in a much more economic way, by comparison with an apparatus in which a detection plate extends over the whole examination width. As a reminder, a 81 µm definition image requires 15241 points per $cm^2$ to be processed. If the image is 50 cm wide and 46 cm high, it requires 35 million points. For a 27 µm definition, it is necessary to process 137174 points per $cm^2$, that is to say 315 million points for the 50 cm×46 cm image. A detection plate capable to carry out such a processing would have a prohibitive manufacturing cost.

Preferably, the dose limiter is driven at a speed identical or proportional to the detector speed $$\frac{U}{N\tau}$$

where U is the useful width of the detector irradiated or illuminated by the beam through the slit of the dose limiter, N is the number of lines of the detector, k is the number of photodiodes par line and $\tau$ is the photodiode charge transfer time of one line to the adjacent line, cumulatively from the first line $l_1$ to the last line $l_N$ of the detector, driven in opposite direction with respect to the charge transfer direction, that is to say in translation from the left to the right if the last line $l_N$ marks a left edge of the detector and the first line $l_1$, a right edge of the detector.

By comparison with a detector having only one line of k photodiodes, the aforementioned detector enables to integrate on the last line $l_N$ the intensity detected in a point of the detector during the duration $N\tau$. This enables to decrease the power of the source proportionally to the integration time $N\tau$, at constant irradiation or illumination dose. In addition, the useful width U is N times greater than a one line detector, at constant definition of detection, i.e. same line width. Driving the dose limiter at a speed identical or proportional with the detector $$\frac{U}{N\tau},$$

DETAILED DESCRIPTION OF THE PREFERRED EMBODIMENT

Figure 1:
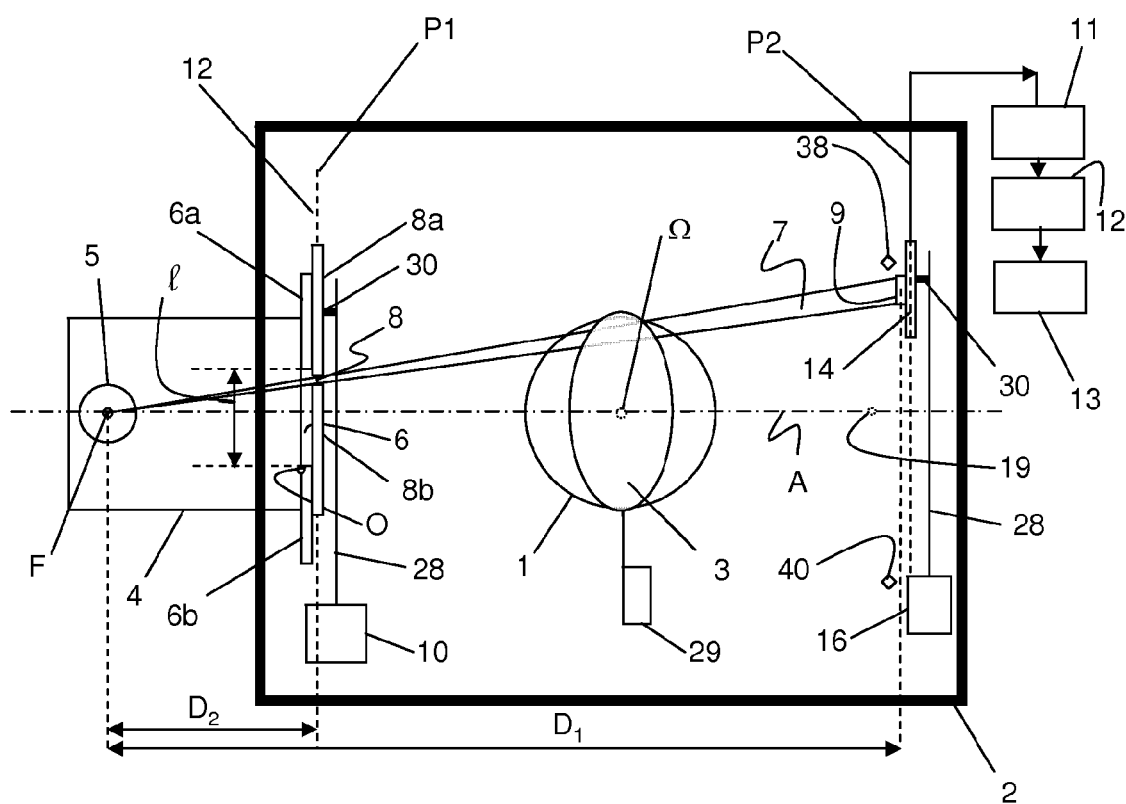
FIG. 1 is a top view of an apparatus according to a first embodiment.

FIG. 1, a first embodiment of an X-ray or infrared imagery apparatus, for radiography or scanning, includes, in a cabin 2:
- a support 1 for receiving a body to be examined 3,
- an X-ray or light ray source 5 provided with a focus for emitting a beam 7 through a slit 8 of a dose limiter 8, 8a, 8b driven in translation to sweep the body,
- a detector 9 driven in translation to be irradiated or illuminated by the beam 7 sweeping the body in order to detect an intensity attenuated along the X-ray or light ray propagation path through the body,
- an analog-to-digital converter 11 to convert the detected intensities into data to determine an X-ray or light ray attenuation due to the body, and
- a programmed computer 13 to process the data resulting from the conversion of the detected intensities in order to obtain an image representing the X-ray or light ray attenuation.

Support 1 rotates around rotation axis Ω, conventionally defining the height direction.

Source 5 is attached in a parallelepipedic box 4 provided with an output section 6 with two edge plates 6a, 6b spaced one from the other by a width l. It should be noted that these two plates slide with respect to box 4 if it is desired to vary the width l of output section 6. Said source 5 emits the beam at focus F placed in an X-rays tube. The respective positions of focus F and plates 6a, 6b determine an axial propagation direction A of the beam outside parallelepipedic box 4. The width l of output section 6 determines the divergence of the beam around axial direction A. The dose limiter includes two coplanar plates 8a, 8b laid out in a plane P1 perpendicular to axial direction A of the beam. The two plates 8a, 8b are spaced one form the other in order to form a slit 8 of width e. The dose limiter is driven in translation in plane P1 by a jack 10 along a rail 12, preferably a ball rail to limit frictions. Movable rod 28 of the jack is attached to plate 8a by a fastener 30. Slit 8 is thus moved in front of output section 6 of parallelepipedic box 4 so that the beam sweeps the body to examine 3. The two plates are out of lead for example. They have a 16 cm width, a 10 cm height and a 2 mm thickness.

Detector 9 is attached to a support 14 driven by a jack 16 along a rail, in translation in a plane P2 perpendicular to axial direction A of the beam. Movable rod 28 of the jack is attached to support 14 by a fastener 30. It should be noted that jack 16 is chosen sufficiently robust if it is desired to move detector 9 without any rail in order to limit frictions and to better control detector speed compared to dose limiter speed.

In accordance with the invention, dose limiter 8, 8a, 8b is driven in translation at a speed proportional with that of detector 9, controlled by the ratio $$\frac{D_2}{D_1}$$

wherein, on the one hand, $D_1$ is the distance between source 5 and detector 9 and, on the other hand, $D_2$ is the distance between source 5 and dose limiter 8, 8a, 8b.

A software is loaded in computer 13 in order to control the translation of jacks 10, 16 moving dose limiter 8, 8a, 8b and detector 9. As an example, dose limiter speed equals the third of detector speed when the distance between source 5 and detector 9 equals 180 cm and the distance between source 5 and dose limiter 8, 8a, 8b equals 60 cm. As the detector moves on 50 cm in order to obtain an image of such a width, the dose limiter moves in the same time on 16.66 cm, in the same direction as the detector. The synchronization between the dose limiter and the detector is carried out independently of the source, which is fixed. This arrangement enables to ignore the source inertia conversely to the case where the source is to be moved by the dose limiter. Indeed, any apparatus requiring the X-ray tube to be rotated implies a difficult step-by-step adjustment of said rotation taking into account that the X-ray tube may weigh as high as 35 kg and that a high tension supply cable and a cooling tube, as an oil cooling tube, have also to be moved. It should be stressed again that the invention enables to easily change the distances between the focus and the detector and between the focus and the dose limiter. It is thus sufficient to adjust the translation speeds of these two elements.

FIGS. 2 to 5 illustrate different executions of the first embodiment. In these executions, the X-ray or light ray beam is a secondary beam 72, resulting from a virtual focus F2 formed by a primary beam 71, emitted by an actual focus F1 supplied with source 5 and reflected by a double reflection reflector 55 laid out between source 5 and dose limiter 8, 8a, 8b.

Figure 2:
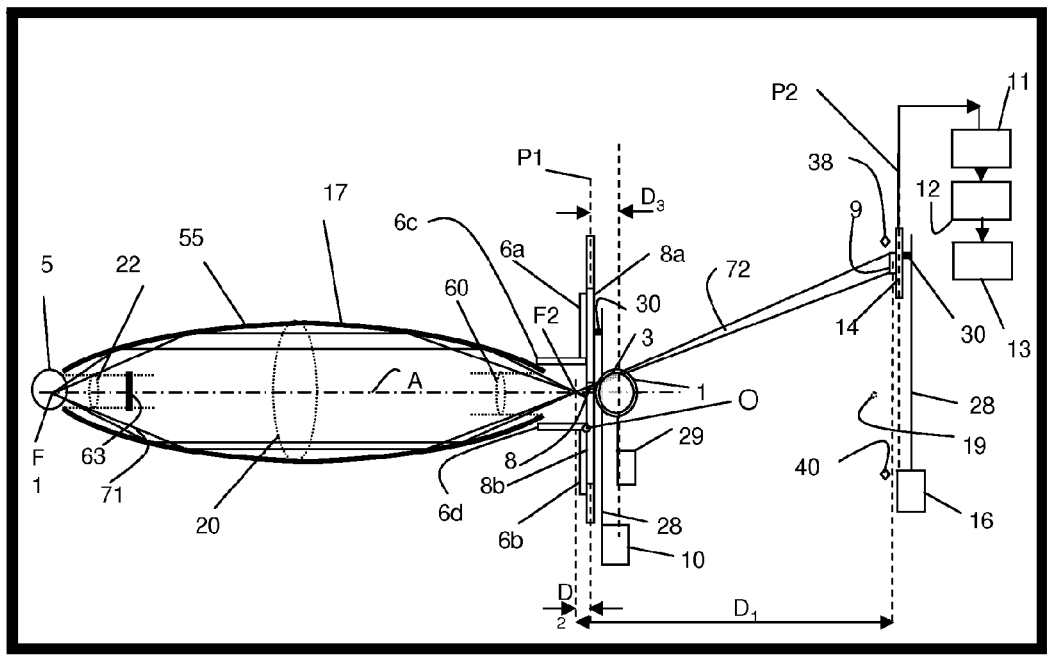
FIG. 2 is a top view of a particular execution of the first embodiment wherein the dose limiter is laid out downstream with respect to a virtual focus obtained by a single axis and double reflection reflector.
Figure 3:
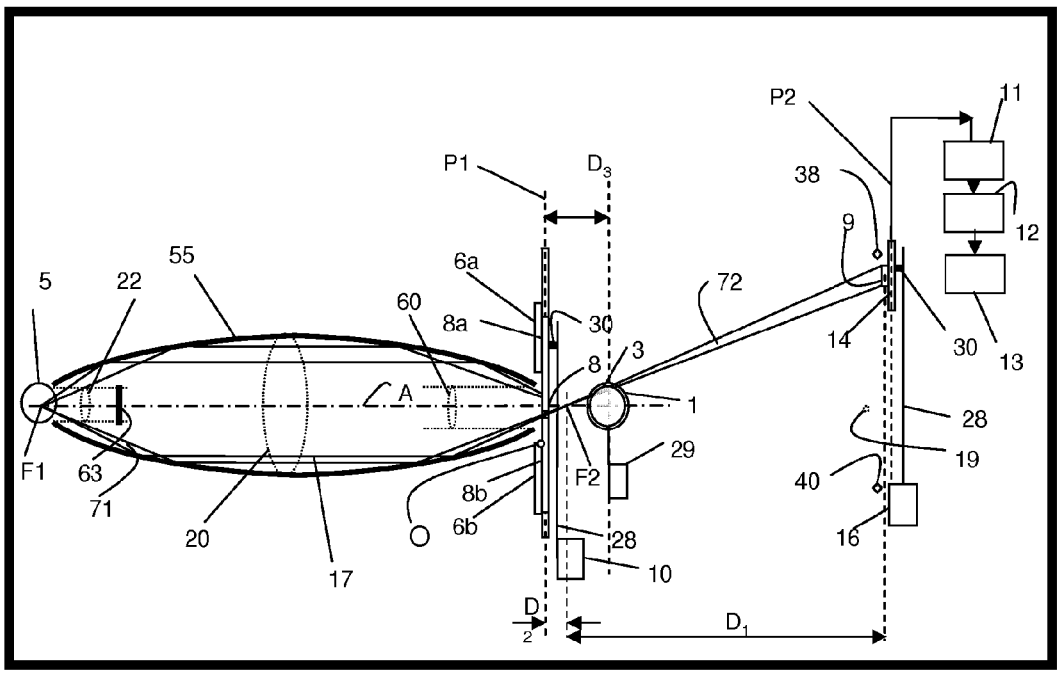
FIG. 3 is a top view of a particular execution of the first embodiment wherein the dose limiter is laid out upstream with respect to a virtual focus obtained by a single axis and double reflection reflector.

FIGS. 2 and 3 particularly illustrate a double reflection reflector 55 whose input section 22 and output section 60 are aligned along axial direction A of the reflector. Preferably, this reflector is a paraboloid of revolution. Actual focus F1 supplied by source 5 occupies the position of the geometric focus of the paraboloid input. X-rays or light rays of the primary beam 71 emitted by actual focus F1 undergo a first reflexion so that they propagate parallel to axial direction A of the reflector and a second reflexion modifying their propagation to converge at virtual focus F2 which occupies the position of the geometric focus of the paraboloid output. X-rays or light rays resulting from virtual focus F2 form the secondary beam 72. A disc-shaped shutter 63 is laid out downstream from the input section 22 of double reflection reflector 55 to stop the propagation of the direct rays emitted by actual focus F1. It should be noted that reflector 55 includes two end-to-tail paraboloids which are movable in translation along axial direction A if it is desired to vary the position of the virtual focus F2 along this axial direction. These two paraboloids also are of two different sizes if it is desired.

Figure 4:
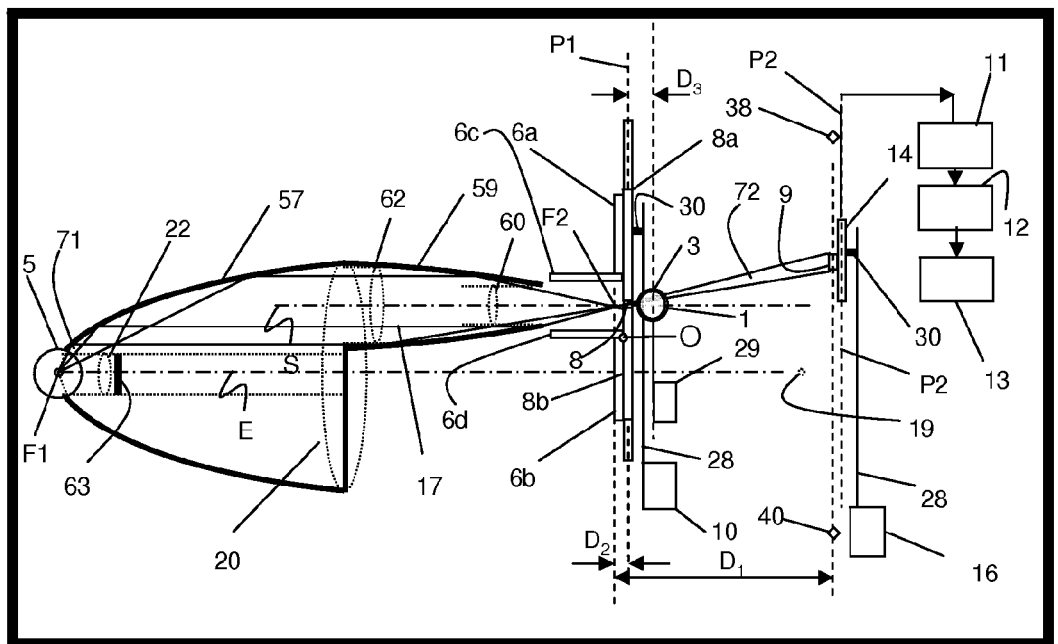
FIG. 4 is a top view of a particular execution of the first embodiment wherein the dose limiter is laid out downstream with respect to a virtual focus obtained by a two axes and double reflection reflector.
Figure 5:
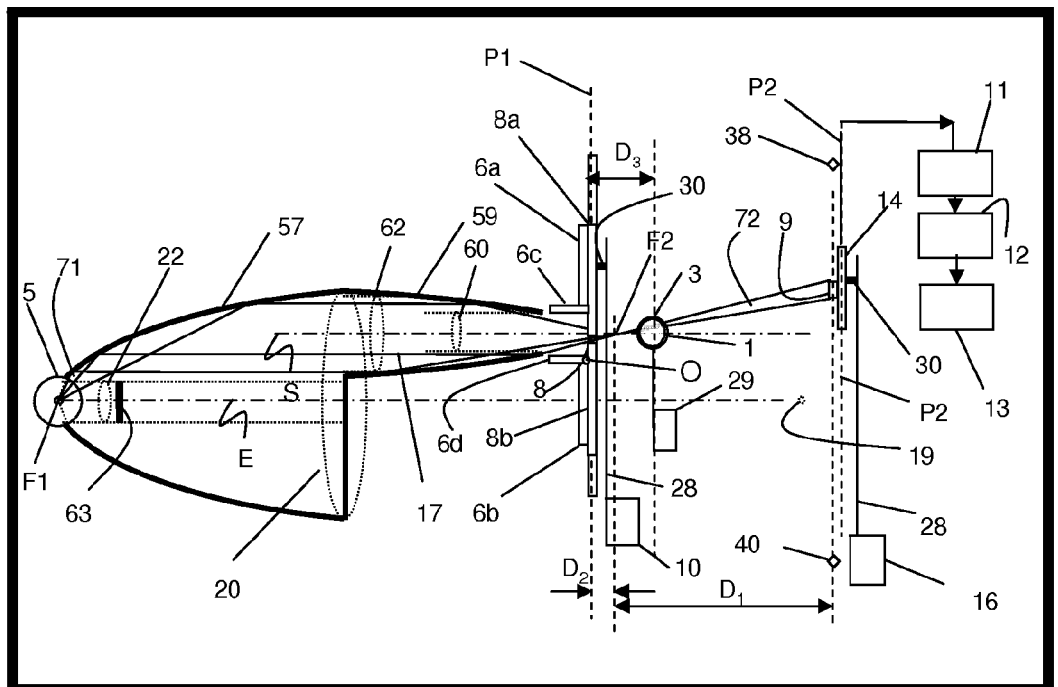
FIG. 5 is a top view of a particular execution of the first embodiment wherein the dose limiter is laid out upstream with respect to a virtual focus obtained by a two axes and double reflection reflector.

FIGS. 4 and 5 particularly illustrate a double reflection reflector 55 whose input section 22 is aligned along a first axial direction E of the reflector and output section 60, along a second axial direction S of the reflector, parallel but non-coaxial with the first axial direction E. Preferably, this reflector includes two end-to-tail paraboloids of revolution 57 and 59. Actual focus F1 supplied by source 5 occupies the position of the geometric focus of input paraboloid 57. X-rays or light rays of the primary beam 71 emitted by actual focus F1 undergo a first reflexion in input paraboloid 57, aligning their propagation parallel to axial direction E. A disc-shaped shutter 63 is laid out downstream from input section 22 of input paraboloid 57 to stop the propagation of the direct rays from actual focus F1. Large section 62 of the output paraboloid 59 preferably lies in the annular region of the large section 20 of the input paraboloid 57 through which the reflected rays propagate parallel to axial direction E. These reflected rays undergo a second reflexion in the output paraboloid 59 that makes their propagation to converge towards virtual focus F2 which occupies the position of the geometric focus output paraboloid 59 along axial direction S. X-rays or light rays resulting from virtual focus F2 form the secondary beam 72.

FIG. 2 or 4, dose limiter 8, 8a, 8b is laid out downstream from virtual focus F2, that is to say between this virtual focus and the body to be examined 3 and is driven in translation in the same direction of movement as the detector at a speed proportional to it, controlled by the ratio of the distances between on the one hand, virtual focus F2 and the detector, referred to as D1, and virtual focus F2 and dose limiter 8, 8a, 8b on the other hand, referred to as D2. FIG. 3 or 5, dose limiter 8, 8a, 8b is laid out upstream of virtual focus F2, that is to say between this virtual focus and the double reflection reflector 55 and is driven in translation in a direction of movement opposed to the detector at a speed proportional to it, controlled by the ratio of the distances between on the one hand, virtual focus F2 and the detector, referred to as D1, and virtual focus F2 and dose limiter 8, 8a, 8b on the other hand, referred to as D2.

The particular executions illustrated by FIGS. 4 and 5 preferably enables to lay out several output reflectors 59 downstream from the input reflector of 57. As a result, a same X-rays or light rays source 5 is used to examine several bodies 3 simultaneously. A set of three distances D1, D2, D3 is associated to each output reflector 59 by adjusting the position of virtual focus F2 or the position of support 1 along axial direction S of every output reflectors. The position adjustment of virtual focus F2 is obtained for example by a more or less substantial translation of output reflector 59 compared to common input reflector 57, parallel to axial direction E. Thus, for a given position of the P2 plane of movement of detector 9, different positions of virtual focus F2 or support 1 allow to obtain different magnifications. It should be noted that different positions of support 1 allow, for two given positions of virtual focus F2 and the plane of movement of detector 9, to obtain different magnifications with same kinematic between dose limiter 8, 8a, 8b and detector 9, taken into account that distances D1 and D2 are constant while distance D3 varies with the position adjustment of support 1. As an example, the following numerical values are used: the input reflector 57 is a 60 cm length paraboloid of parameter $\rho=2$. Its large section 20 is 31 cm in diameter. The output reflector 59 is a 30 cm length paraboloid of parameter $\rho=0.1$. Its large section 62 is 4.9 cm in diameter.

The particular executions of the first embodiment which embody a virtual focus enable to sweep the body to be examined 3 with the secondary beam 72 while limiting the X-ray or light ray exposure to the just necessary irradiation or illumination of the detector. These particular executions are quite well adapted to examine small size bodies, from a few centimeters, as in the case of small laboratory animals, to a few millimeters or even micrometers, as in the case of human, animal or vegetal cell tissues. If it is desired, the body 3 is highly brought closer to virtual focus F2 to minimize the distance D3 between them, compared to existing distance D1 between virtual focus F2 and detector 9. Thus, the cell tissue projected image on detector 9 is enlarged in the ratio of the distances D1 and D3.

Pursuant to the executions illustrated by FIGS. 2 and 4, a cell cluster to be examined 3 is laid out in a test tube 1 used as support, at a 4 mm distance D3 from virtual focus F2, so that 250 times magnification is obtained by laying out detector 9 at 1 m (D1=1 m) from virtual focus F2. If a 25 μm resolution detector 9 is used, one obtains an image resolution of cell tissues equal to 100 angströms. The executions illustrated by FIGS. 3 and 5 enable to bring the test tube even closer to virtual focus F2, for example at 1 mm (D3=1 mm), taking into account that dose limiter 8, 8a, 8b is laid out upstream of virtual focus F2. As a result, a 1000 times magnification and a 25 angströms image resolution of cell tissues are obtained by laying out detector 9 at 1 m (D1=1 m). In these different figures, dose limiter 8, 8a, 8b is driven in translation in the P1 plane at a 405 μm/s speed when it is laid out at 5 mm (D2=5 mm) from virtual focus F2 and detector 9 is moved in the P2 plane at a 8.1 cm/s speed. Slit 8 of the dose limiter is reduced at a 50 μm width. Jack 10 for moving the dose limiter here is replaced by a piezoelectric actuator toothed rack, whose example is disclosed by European patent application EP-A-1058322 and U.S. Pat. No. 6,429,572 filed by the applicant.

The particular executions of the first embodiment which embody a virtual focus apply to the imagery of any body, living or inanimate. In the case of living bodies, metallic sheets, for example out of aluminium or iron, are arranged around the body to further reduce the X-ray exposure by the absorption of part of the emitted dose, which turns to be high near the virtual focus.

Figure 6:
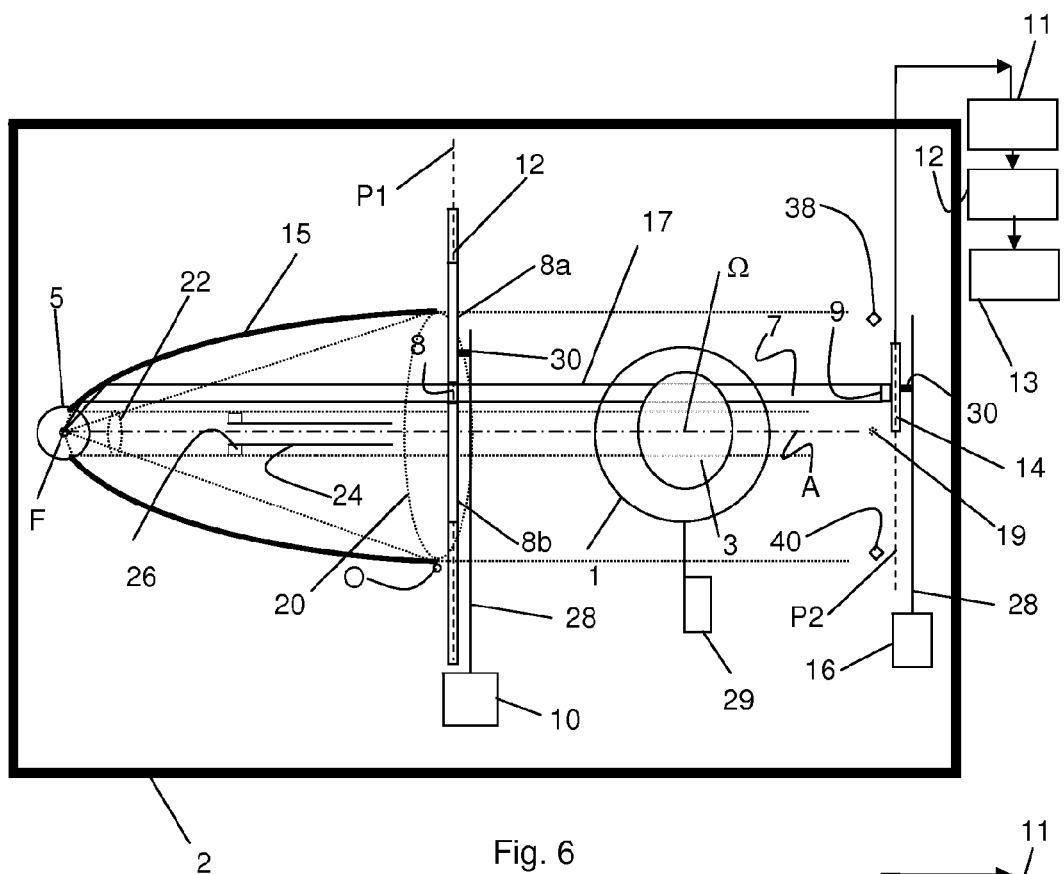
FIG. 6 is a top view of an apparatus according to a second embodiment, for a first sweep position.
Figure 7:
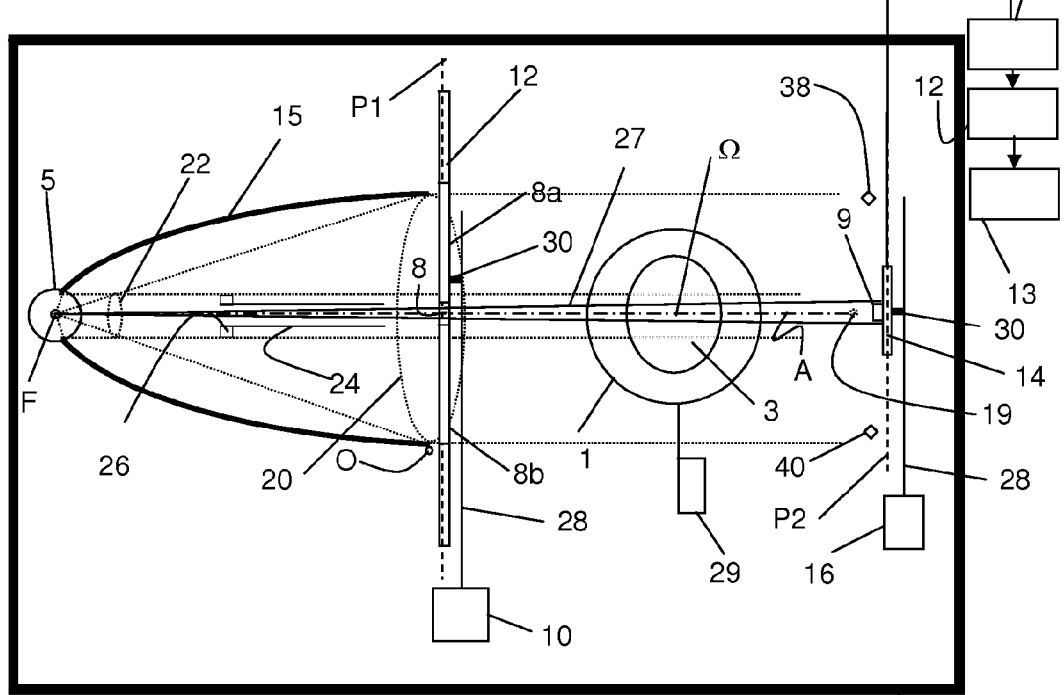
FIG. 7 is a top view of an apparatus according to a second embodiment, for a second sweep position.

FIGS. 6 and 7 illustrate a second embodiment of the invention. In these figures, the elements in common with the first embodiment carry the same references and are regarded as described by reference to FIG. 1.

A reflector 15 is laid out in front of focus F of source 5. In grazing incidence, emitted X-rays by source 5 are completely or partially reflected by the walls of reflector 15. One determines the angle θ below which the reflexion is complete by the following formula:

$$\theta < \lambda/(5*10^{-8})$$

Wavelength λ and supply tension V are related by the following formula:

$$V(kV) = 12.38/\lambda(Ang)$$

The calculation leads rapidly to the following results:
for 125 kV θ=1.12°
for 70 kV θ=2
for 35 kV θ=4°

Reflector 15 preferably is a paraboloid of revolution to parallel the reflected rays in a cylindrical beam. As a reminder, a parabola is defined by a function:

$$y^2 = 2*\rho*x$$

The parameter ρ determines the output section 20 of the paraboloid of revolution. As an example, when parameter ρ is 1, the output section is a 10 cm circle in diameter measured at 50 cm from the paraboloid focus. The body 3 is thus irradiated or illuminated within a 20 cm circle in diameter centred on the projection of focus F on detector 9.

If focus F of the X-ray tube occupies the position of the focus of the parabola which generates the paraboloid, the completely reflected or reverberated rays 17, FIG. 6, are parallel to direction axial A of the beam, that is to say with the paraboloid central axis.

The reflexion or reverberation conditions depend on the angle of an incident ray with the tangent to the parabola at the point of incidence. For ρ=1 and V=75000 volts, the reflexion angle on the surface of the reflector, calculated from the tangent at the considered point, results in a total reflexion if the angular values are lower than 2°. The reverberation rate is a measurement of the ratio between the partial reflexion and the theoretical complete reflexion. This rate generally is acceptable for angles lower than 10°.

This second embodiment distinguishes from the first one by the fact that dose limiter 8, 8a, 8b is driven in translation at the same speed than detector 9, in front of output section 20 of reflector 15, in order to irradiate or illuminate the body 3 with the rays emitted by source 5 and reflected in parallel webs.

A software is loaded on a computer 13 in order to control the translation of the two jacks 10, 16 so as to move dose limiter 8, 8a, 8b and detector 9 at a same speed. If the detector moves 50 cm, the dose limiter moves same distance in the same time.

FIG. 6 shows the apparatus according to the second embodiment in a sweeping position for which detector 9 is irradiated or illuminated by the sole reflected rays 17 passing through slit 8 of dose limiter 8, 8a, 8b parallel to axial direction A of beam 7. In this sweeping position, the direct rays, i.e. the rays that are not reflected by reflector 15, which pass through slit 8 of dose limiter 8, 8a, 8b are misaligned compared to the alignment of slit 8 and detector 9, parallel to axial direction A of the beam, so that they do not reach detector 9.

FIG. 7 shows the aforementioned apparatus in a second sweeping position for which detector 9 is irradiated or illuminated by the sole direct rays 27 passing through slit 8 of dose limiter 8, 8a, 8b.

The transition zone from the sweeping by the reflected rays to the sweeping by the direct rays is determined by input section 22 of parabolic reflector 15. It may happen that the detector is irradiated at the same time by reflected rays 17 and direct rays 27 when slit 8 enters or leaves the area corresponding to input section 22 of parabolic reflector 15. To limit this effect, it is provided to lay out in the parabolic reflector a collimating tube 24 coaxial with the paraboloid central axis and attached to a perforated disc 26 which coincides with input section 22 of parabolic reflector 15. The collimating tube 24 concentrates the direct rays 27 on slit 8 of dose limiter 8a, 8b when it is moved in front of the area which corresponds to input section 22 of parabolic reflector 15. Collimating the rays increases the intensity of the outgoing beam from the collimating tube 24 by the capture of the direct rays at the tube input and their reverberation inside the tube.

By comparison with an apparatus not comprising a dose limiter, the irradiation or illumination dose received by the body t during the corresponding sweeping of detector 9, is divided by the surface ratio of slit 8 of the dose limiter and the output section 6 of parallelepipedic box 2 or 20 of reflector 15.

Figure 8:
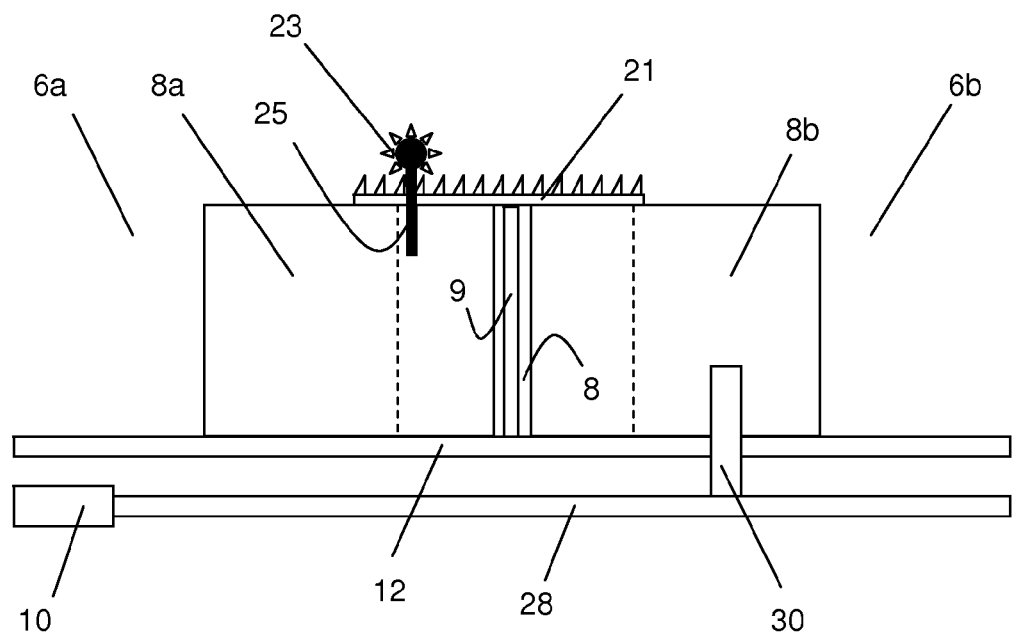
FIG. 8 is a front view of the dose limiter of the apparatuses illustrated by FIGS. 1 to 5.

FIG. 8 illustrates a preferred arrangement of dose limiter 8a, 8b in which the two plates 8a, 8b move one compared to the other if it is desired to adjust of the width e of slit 8. A moving means includes a toothed rack 21 attached to one 8b of the two plates and a notched wheel 23 hold by an axis 25 attached to the other plate 8a to engage with toothed rack 21. It is also provided to adjust the slit width e via a screw engaged with two threads integral with the two plates. The adjustment of the slit width determines a local over-exposure factor defined by the width of the projection of the dose limiter slit 8 on detector 9, compared to the useful width of the detector.

Figure 9:
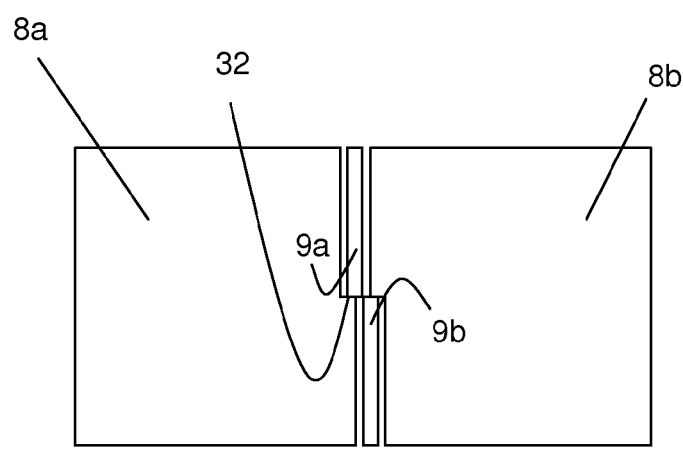
FIG. 9 is a front view of a particular execution of the dose limiter illustrated by FIG. 8.

FIG. 9 illustrates a preferred arrangement of detector 9 provided with two detection rods 9a, 9b to double the image shot height. The two rods 9a, 9b preferably are shifted one compared to the other to avoid the formation of a neutral area in the image due to a defect of height adjustment. In this case, the plates of the dose limiter 8a, 8b are provided with a slit profile 32 corresponding to the shift of the two detection rods to maintain a constant width slit in front of the first 9a detection rod as well as the second detection rod 9b. As a result, the local over-exposure factor is not increased by the shift of the two detection rods.

In the first or second embodiment, dose limiter 8, 8a, 8b preferably is driven in translation by jack 10 starting from a rest point O for which slit 8 is outside output section 6 of parallelepipedic box 4 or output section 20 of reflector 15 to completely close beam 7. In the execution illustrated by FIGS. 2 to 5, the rest point corresponds to a position of slit 8 apart from output section 60 of the double reflection reflector 55. If the dose limiter is laid out at a given distance from output section 60 of the double reflection reflector 55, it is provided to confine the beam between output section 60 and the dose limiter. A tube 6c, 6d extends parallel to the beam axial direction A and is attached to the two walls 6a, 6b spaced by a width l and laid out in the P1 plane. The dose limiter 8a, 8b is moved in translation in the P1 plane closest to the walls 6a, 6b to close the beam when slit 8 is in the rest position O.

In practice, it is provided that the detector begins to move in translation starting from the point corresponding to the projection of dose limiter rest point O on the P2 plane, or begins to move in translation after a delay compared to the dose limiter translation, which corresponds to the time period for the slit 8 to enter the output section of parallelepipedic box 4 or the output section 20 of reflector 15, starting from the rest point O. This arrangement enables to operate the source 5 without to turn it off then on and thus decreases dead times between two image shots. This also assumes a great economical importance, insofar a continuously operated source has an increased life duration. On the contrary, to turn on and off the source repeatedly would fast lower the characteristics of the X-ray tube.

Figure 10:
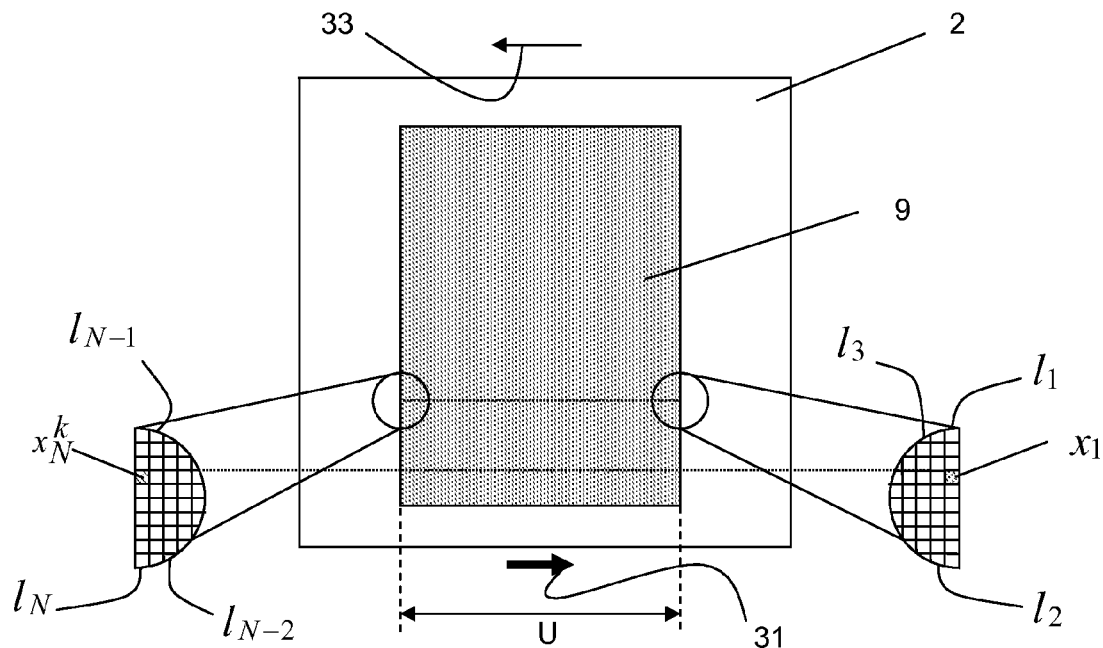
FIG. 10 is a front view of the detector of the apparatuses illustrated by FIGS. 1 to 5.
Figure 11:
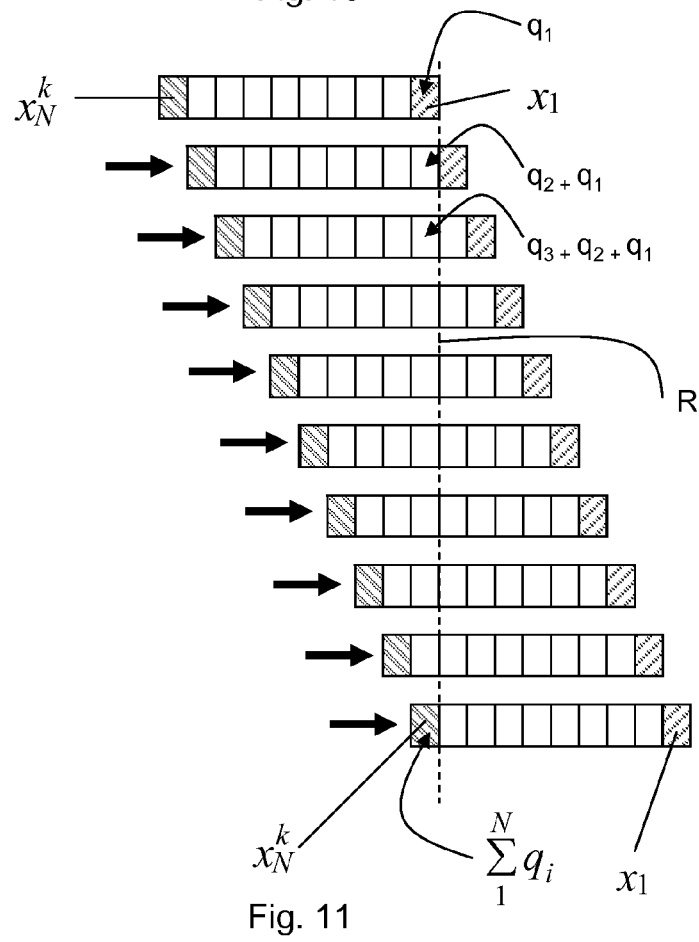
FIG. 11 represents a segment of the detector illustrated by FIG. 10, at different times during the translation of the detector.

FIGS. 10 and 11 illustrate an embodiment wherein a detector 9 comprises N lines and wherein every line is provided with k photodiodes $x_n^k$. The line number N determines the definition of the detector whose useful width is U. The charge of the photodiodes that all have the same index k is transferred from one line to the adjacent line, cumulatively from the first line $l_1$ to the last line $l_N$ of detector 9, with a transfer time τ.

FIG. 11, charge $q_1$ accumulated during τ by photodiode $x_1^k$ is transferred to photodiode $x_2^k$. Within the same time, photodiode $x_2^k$ moves with detector 9 to occupy, in a fixed referential R compared to cabin 2, the position which was occupied by photodiode $x_1^k$ before the transfer. Photodiode $x_2^k$ accumulates a new charge $q_2$ during τ and transfers the cumulated charge $q_1+q_2$ to photodiode $x_3^k$. Within the same time, photodiode $x_3^k$ moves with the detector translation to occupy, in a fixed referential R compared to cabin 2, the position which was occupied by photodiode $x_2^k$ before the charge transfer. Photodiode $x_N^k$ that has the same k index and belongs to the last line cumulates, at the end of the N charge transfers, the sum of the charges accumulated by every photodiode having same index k during each transfer τ.

Each photodiode of the last line $l_N$ thus integrates the intensity corresponding to the irradiation or the illumination of the body to examine 3 by a same X-ray or light ray during the duration of the charge transfer from the first line $l_1$ to the last line $l_N$, that is to say during Nτ, when detector 9 is moved at speed $$\frac{U}{N\tau}$$

in opposite direction to the charge transfer. FIGS. 6 and 7, the detector is conventionally moved from the left to the right as indicated by arrow 31, whereas the charges of the photodiodes that all have a same index k move, as indicated by arrow 33, from the last line $l_N$ at a left edge of detector 9, to the first line $l_1$ at the right edge of said detector 9.

The irradiation dose of the body is proportional to the source power and the exposure duration. To obtain an image under a same definition, for example 27 μm, with a same irradiation dose, integration during Nτ enables to divide by Nτ the source power. The charge transfer detector also enables to decrease the aforementioned local over-exposure factor, since the useful width of the detector is N times greater, compared to that of a detector with only one detection line.

Figure 12:
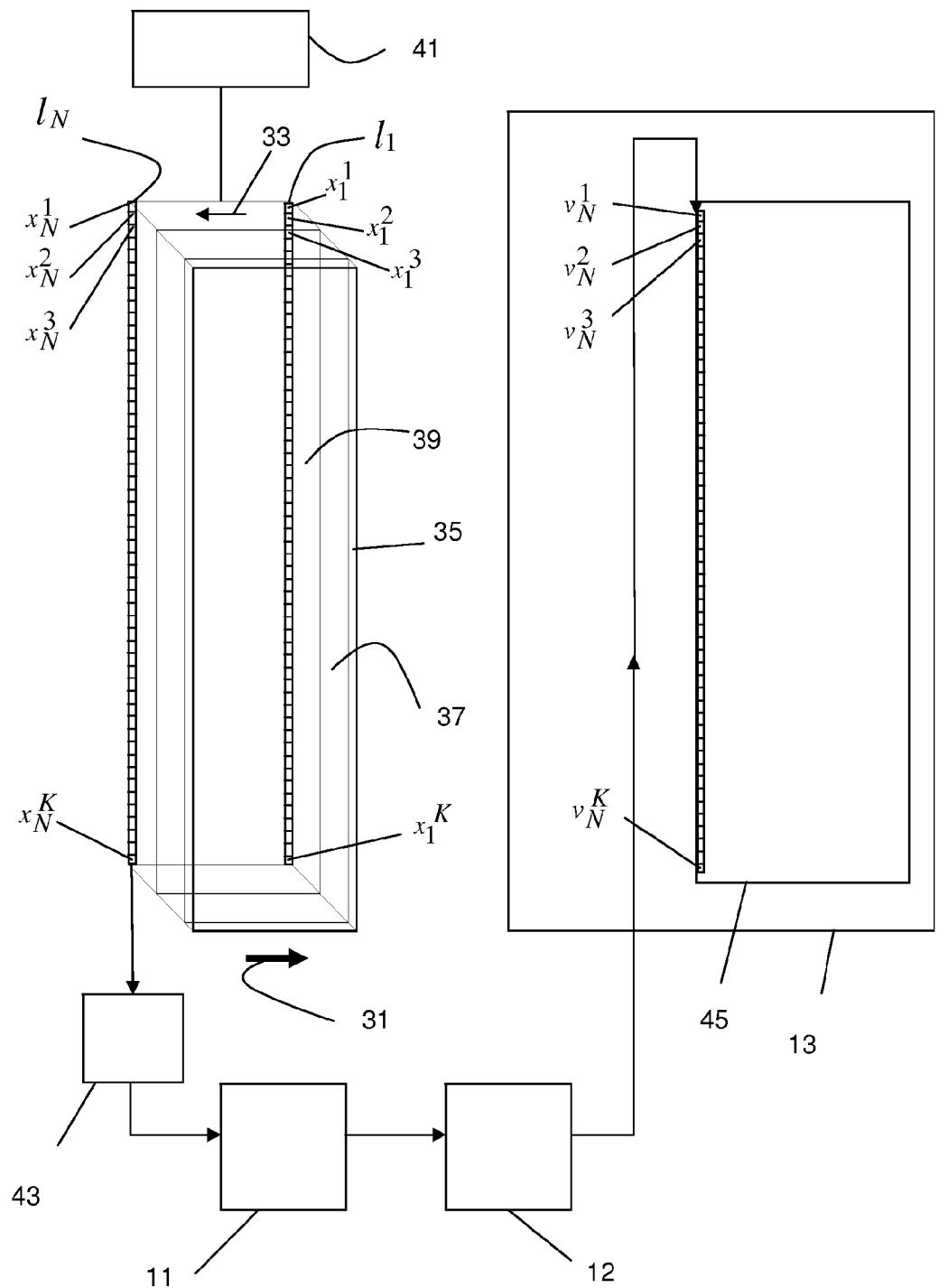
FIG. 12 schematically shows the structure of the detector as well as the data acquisition chain of the apparatuses illustrated by FIGS. 1 to 5.

FIG. 12 schematically shows the structure of detector 9 as well as the elements of the acquisition chain.

Detector 9 includes a scintillator 35, an optical fibre array 37 and a photodiode sensor 39 provided with N lines of k photodiodes. The X-rays cause the scintillator 35 to emit packets of infrared photons which are guided by the optical fibres 37 until illuminating the photodiodes. A phase generator 41 is coupled with detector 9 to carry out on the one hand, the charge transfer of the photodiodes $x_1^1, x_1^2, x_1^K$ of the first line $l_1$ to the photodiodes $x_N^1, x_N^2, x_N^K$ of the last line $l_N$, according to the method described previously, and the transfer of the last line $l_N$ towards an amplifier 43 then towards the analog-to-digital converter 11. A 8 or 12 bit conversion is used.

It should be noted that detector 9 and amplifier 43 are cooled by nitrogen at −160° C.-190° C. if it is desired to decrease the background noise which is thermal in origin and to increase the amplifier gain. In the same way, phase generator 41 is cooled at −20° C. The cooling of detector 9, phase generator 41 and amplifier 43 increases the acquisition chain sensitivity and thus contributes to reduce the irradiation dose.

An interface 12 is provided for between analog-to-digital converter 11 and computer 13 to transfer, at a frequency equal to the inverse charge transfer time $\tau^{-1}$, the data $v_N^1, v_N^2, v_N^K$ resulting from the conversion of the cumulated charges of every photodiode $x_N^1, x_N^2, x_N^K$ of detector last line $l_N$. The data are stored in the computer memory in form of a table 45 which represents the image obtained as the dose limiter 8a, 8b moves at a speed, proportional or identical to detector 9, during the sweeping of the body.

A detector in conformity with the detector aforementioned is available under the trademark ATMEL and reference AT71957M. The number of lines N is equal to 242 and each line has 8520 photodiodes. The detector is shaped in a detection rod having a useful width U equal to 0.654 cm and an useful height equal to 23 cm. Each line has a 27 μm definition in width as in height. The charge transfer time τ is equal to 1 ms. As the detector moves 50 cm, the irradiation dose is divided by 76.45 if the projected width of dose limiter slit 8 on detector 9 is equal to the useful width of the detector, that is to say 0.654 cm. For a projected width equal to 1 cm, the dose is divided by 50 and the local over-exposure factor equals 1.53. Dose limiter 8a, 8b is moved in opposite direction to the charge transfer, at speed $$\frac{U}{N\tau}$$

equals to 2.7 cm/s. X-ray or infrared ray exposure time Nτ of any part of the body is limited to 242 ms. It is possible to electronically gather the photodiodes of three adjacent lines to pass from a definition of 27 μm to a definition of 81 μm. Detector 9 is then moved at a speed equal to 8.1 cm/s and the exposure duration of any part of the body decreases at 80 ms.

The X-ray or infrared imagery apparatus according to the invention applies to radiography or scanning. In radiography, generally two shots of the body are taken, that is to say a face shot and a profile shot. In scanning, different shots under different angles of rotation are taken to obtain an image of the attenuation coefficients of the body in sectional planes perpendicularly to the rotation.

In the following, the description is limited to the use of the apparatus in the scanning field. French patent application FR 2888374 and international application WO 2007/006560 filed by the applicant serve as references for the underlying principle of the scanning method as well as for a comprehensive disclosure of the so-called direct generation scanning method to which reference is made from now on. French patent application FR 2871911 and international application WO 2006/003312 filed by the applicant also serve as references for a scanning method involving matrix amplification and point by point adjustment.

The device is particularly defined by the fact that during data acquisition, support 1 is driven in rotation around the axis of rotation Ω, by a motor 29 and the fact that computer 13 is programmed to carry out the following steps:
(1) to build a column generating vector and a line generating vector whose n and m terms respectively consist in data $c_i$ and $\rho_j$ resulting from the conversion of detected intensities at a same point $x_N$ of detector 9 during its translation and respectively for a first i and a second j angles of rotation, preferably orthogonal, of support 1 around the axis of rotation Ω, said $c_i$ and $\rho_j$ data corresponding to a grid of n×m elementary areas of the body sectional plane which is perpendicular to the axis of rotation Ω and contains the considered point $x_N$ of detector 9, (2) to build an initial matrix (n, m) with the terms of the two generating vectors, by assigning to each elementary area a line and column term Bij which represents an attenuation coefficient and is equal to the half sum of the homologous term $c_i$ of the column generating vector divided by the number m of terms of the line generating vector and the homologous term $\rho_j$ of the line generating vector divided by number n of terms of the column generating vector, $$B_{ij} = \frac{1}{2}\left(\frac{\rho_j}{n} + \frac{c_i}{m}\right)$$

(3) to adjust the attenuation coefficient of each elementary area by using the following formula:

$$C_{ij} = \frac{\rho_j}{n} + \frac{c_i}{m} - \frac{1}{2nm}\left(\sum_{i=1}^{n} c_i + \sum_{j=1}^{m} \rho_j\right)$$

where, in this formula,
Cij=the desired value of the attenuation coefficient of the elementary area (i, j) of the grid
Bij=the initially estimated value
(n)=the line number of the initial matrix
(m)=the column number of the initial matrix
$\rho_j$ is term j of the line generating vector
$c_i$ is term i of the column generating vector
to obtain an image of the body sectional plane for the first and second angles of rotation, corresponding to an adjusted matrix for which the line and column border values calculated using the adjusted values (Cij) are respectively equal, for every lines and every columns, to the terms of the line and column generating vectors:

$\Sigma_{j=1}^{m} Cij = c_i$ $\Sigma_{i=1}^{n} Cij = \rho_j$ (4) to repeat steps (1) to (3) with data acquired for different pairs of angles of rotation to respectively obtain different adjusted matrixes corresponding to different images of the body sectional plane for the different pairs of angles of rotation,
(5) to use a rotation operator to superimpose all the adjusted matrixes on a same pair of angles of rotation, and
(6) to display on the screen of the computer a synthesis image of the body sectional plane corresponding to a synthesis matrix of the attenuation coefficients of every elementary area (i, j) of the grid, obtained by a term to term average of all the adjusted and superimposed matrixes.

FIG. 10, the considered point $x_N$ of detector 9 consists for example in photodiode $x_N^k$ having the number k in the last line N of detector 9. Data $c_i$ result from the intensities detected by this photodiode throughout the translation of detector 9, for a angle of rotation i of support 1 around the axis of rotation. In the same way, data $\rho_j$ result from the intensities detected by this photodiode throughout the translation of detector 9, under the angle of rotation j, rotated 90 degrees with respect to angle of rotation i.

When, according to the second embodiment of the invention, photodiode $x_N^k$ is irradiated at the same time by rays 17 reflected by the paraboloid reflector and by direct rays 27 or rays collimated by collimating tube 24, data $c_i$ or $\rho_j$ resulting from the intensities detected by this photodiode for angle of rotation i or j are over-estimated. Taking into account that during rotation of support 1 around the axis of rotation Ω, a same elementary area of the body 3 is only placed in front of photodiode $x_N^k$ for angle of rotation i or j, the term to term average carried out at step (6) of the method tends to smooth the overestimation effect. Depending on the standard deviation of the average obtained, overestimated data are clipped if desired.

To obtain an image comprising (m×n) points of the body 3 in the sectional plane P, steps (1) and (2) build a (m×n) terms initial matrix by estimating every term of the column and line generating vectors starting from data obtained after only two irradiations of the body for two angles of rotation, preferably orthogonal.

At step (3), the estimated terms of the initial matrix are adjusted with respect to the n and m detected intensity average values and taking into account the border values. A first adjusted matrix which corresponds to a first adjusted image is thus obtained.

In practice, steps (2) and (3) are carried out in a single step referred to as direct generation step which enables to directly generate the desired attenuation coefficient values Cij of the image of the body sectional plane for the first and second angles of rotation. The formula used at step (3) indeed only requires the knowledge of data $c_i$ and $\rho_j$ resulting from the detected intensities in the strip of the detector for the first and the second angles of rotation. The third term $$\frac{1}{2nm}\left(\sum_{i=1}^{n} c_i + \sum_{j=1}^{m} \rho_j\right)$$

is constant and is calculated only once for all the desired values Cij. The elementary calculations involved by the formula leads to a high gain of calculation time. Furthermore, the Cij terms of an image are calculated independently from another image, meaning that no retro-projection occurs between two successive images obtained for two pairs of rotation angles. The synthesis image simply is obtained by a term-by-term average of the Cij values of the all images obtained for the different pairs of angles of rotation. This means a significant reduction of the calculation errors.

The preceding general description applies to a small size body examined according the previously described particular executions of the first embodiment of the scanning apparatus provided with a virtual focus. Support 1 is for example a test tube driven in rotation around the axis of rotation Ω. Image resolutions of 100 or 25 angströms open the path to an examination of cell constituents, especially to a comparison between the cell nucleus volume and the cytoplasm volume in the perspective of characterizing cancerous cells.

The different image shots have to be centred on a same frame of reference. In the apparatus in accordance with the invention, wherein the detector is driven in translation over a relatively large width, the centring of the image shots compared to the detector translation may involve inaccuracies as the detector weight or speed is higher. It should be noted that the unit consisting in jack movable rod 28 and detector 9 is a 15 kg mass approximately. This is the reason why an image shot centring system independent of the detector translation is preferred.

Figure 13:
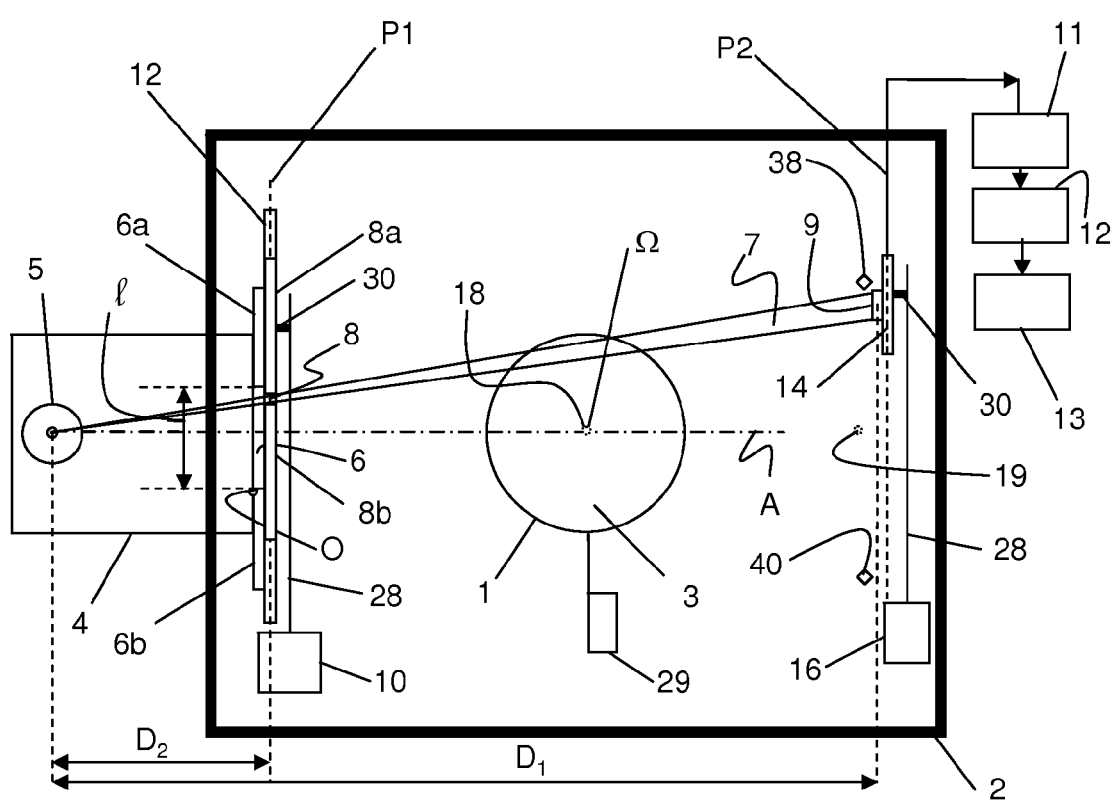
FIG. 13 is a top view showing an image shot centering device.

FIG. 13, the image shot centring system includes a fixed mark 38 compared to detector 9 and a lead wire 18 which is suspended on the ceiling of cabin 2. Fixed mark 38, for example a tip, is laid out in front of the P2 plane in which detector 9 moves, in an area outside the projection of the body 3, i.e. offset compared to axial direction A of the beam. The lead wire 18 is laid out directly above the rotation centre of support 1 in the absence of a body to indicate the rotation axis. FIG. 10, projections 34 and 42 respectively of the lead wire 18 and the fixed mark 38 are recorded during an image shot 47 which is used as a reference. The position of the lead wire projection is then determined compared to the fixed mark projection and recorded as a position of the projection of rotation axis Ω. Any image shot taken after the removal of the lead wire 18 is thus centred on the rotation axis Ω compared to the fixed mark projection 42.

The parallelism between detector 9 and the axis of rotation Ω, i.e. the verticality of detector 9, is controlled by means of a single lead wire. If a parallelism defect occurs it is corrected by acting on the inclination of jack 16. It should be kept in mind that jack 16 is likely to undergo, after many manipulations, a slight inclination involving a verticality defect of detector 9. The centring system also includes if desired a second fixed mark 40, homologous of the first fixed mark 38, to control the parallelism between detector 9 and the axis of rotation Ω. Marks 38 and 40 are laid out at two different heights along the axis of rotation Ω.

Figure 14:
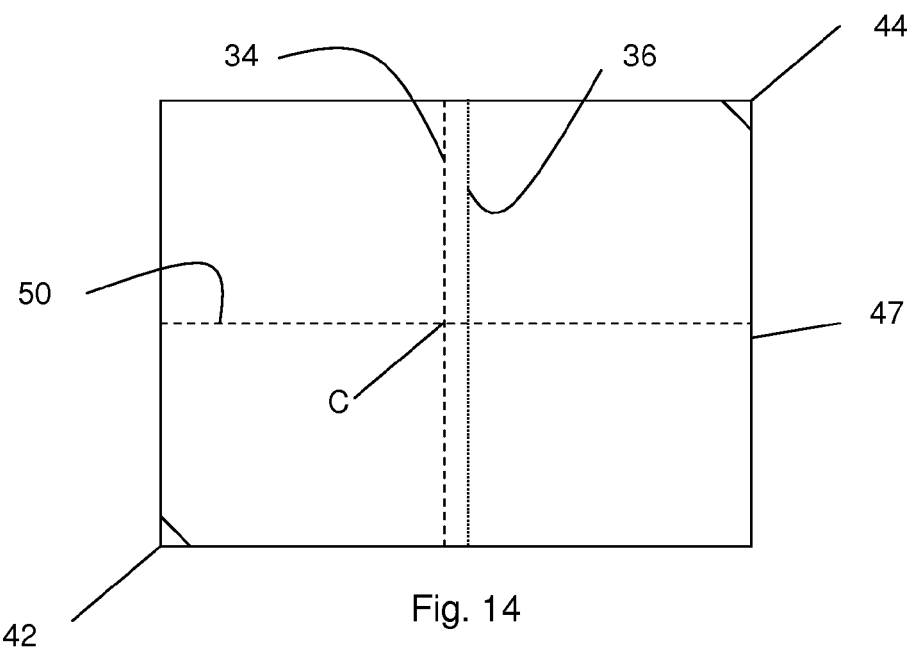
FIG. 14 illustrates centering implementation by means of a first reference image shot.
Figure 15:
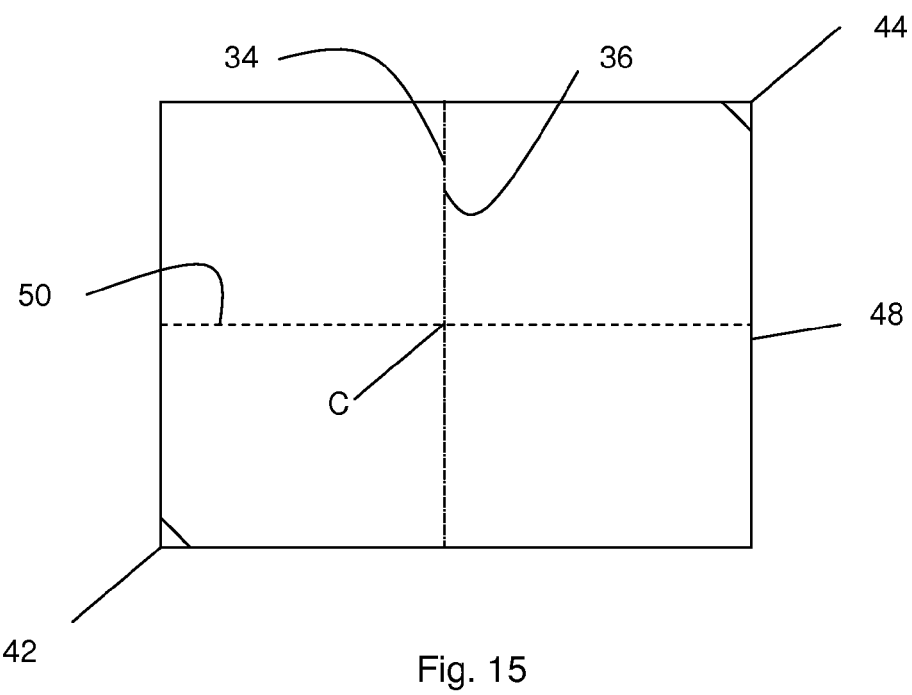
FIG. 15 illustrates centering implementation by means of a second reference image shot.

It should be noted that the centring system includes if desired a second lead wire 19 laid out in front of the P2 plane in which the detector 9 moves, in an adjustable position. Before centring, it has an approximate position between source focus F and the axis of rotation Ω indicated by the suspended first wire 18. FIG. 14 shows the image shot 47 used as a reference, wherein projections 34 and 36 respectively of first wire 18, indicating the axis of rotation Ω, and of second wire 19 are shifted one compared to the other. The position of second wire 19 at the ceiling cabin is then adjusted so as to exactly align said second wire 19 with source focus F and the suspended first wire 18. The alignment is controlled by a second image shot 48 used a reference wherein, FIG. 15, projections 34 and 36 of the two suspended wires 18 and 19 exactly match.

The second lead wire 19 holds the projection of the axis of rotation Ω on the detector and consequently on any image taken after the removal of the suspended first wire 18. This enables to centre the different image shots on the axis of rotation Ω indicated by the projection of the suspended second wire 19.

First wire 18 is for example out of copper. Second wire 19 is preferably more X-ray absorbent than first wire 18 and is for example out of gold alloy. Such an alloy also enables to use a finer wire, for example 0.6 mm in diameter. However, the second lead wire 19 is hidden by the body 3 in some cases and this is the reason why the centring system using the fixed mark 38 laid out outside the projection of the body 3 is preferred.

The apparatus according to the invention also includes if desired a horizontally centring means, i.e. perpendicularly to the axis of rotation Ω. Said horizontally centring means consists for example in a rod which is laid out in the parallelepipedic box 4 or the collimating tube 24. FIGS. 10 and 11, projection 50 of the rod on the image shots 47 and 48 used as references is marked compared to the projection 42 of the fixed mark 38. The intersecting point between rod projection 42 and lead wire projection 34 indicating the axis of rotation Ω determines the centre C of any image shot. Said centre C indicates the projection of source focus F. Starting from centre C, data resulting form the conversion of the detected intensities are corrected to take into account the distance change between focus F and a photodiode of detector 9 at any moment of its translation. As a reminder, X-ray intensity decreases proportionally to inverse square propagation distance.

The X-ray or infrared imagery apparatus according to the invention enables high definition images to be obtained, that is to say 27 μm multiple definition, while limiting at minimum patient or technicians exposure.

Tests carried out led to the following results:
i) adjusting the dose limiter slit width at 2 cm enables a 1.725 milligrays average dose to be obtained on the patient.
ii) adjusting the dose limiter slit width at 0.5 cm enables a 0.0983 milligrays average dose to be obtained on the patient. In this case, measurements carried out around the cabin give values comparable with natural radioactivity.

With regard to the patient, the received dose depends on the source power which is necessary for the X-rays to pass through the body part to be examined. One foresees today:
iii) a 0.5 cm slit width enabling a 0.5 milligrays dose to be received by a wide body part, for example thorax.
iv) a 0.5 cm slit width enabling a 0.090 milligrays dose to be received by a narrow body part, like hand.

Depending on the image shot number necessary to obtain the synthesis image, the total dose received by the patient varies between 1 and 6 milligrays. It should be noted that the parabolic reflector, according to the second embodiment, enables the received dose to be further decreased with a same source power.

It is also essential to underline that the use of an apparatus according to the invention enables low X-ray exposure durations. For a wide body part, like thorax, the acquisition time of a 45 cm width and 30 cm height view equals 5.55 seconds. Total time to carry out a 18 view scanning adds up to 190 seconds, taking into account dead times due to the support rotation, or 380 seconds for a 36 view scanning.

It is also necessary to highlight the data processing low calculating times. A cabin comprising 4 systems source-dose limiter-detector adding up to 184 cm height enables a complete scanning of a patient to be obtained in only one operation with the following times:
v) 361 seconds at a 162 μm definition, if the detector translation is assumed to be the same whatever the examined body part, so that numerous data are recorded for empty areas.
vi) 117 seconds at a 81 μm definition, if the translation of every four detectors is assumed to be adjusted to the width of the body explored by every detector.

As already mentioned, the data processing enables a synthesis image to be obtained at any multiple definition of the detector definition, for example 27 μm. The imagery apparatus according to the invention thus offers to a physician several protocols, among which:
- to choose the detection definition, either 27 μm on every N line of the detector or 81 μm on the third of these lines gathered by three,
- to choose the synthesis image definition, multiple of the detection definition, that is to say 81 μm, 162 μm, 324 μm, or 648 μm, according to the size of the examined part,
- to zoom on a more precise part of the synthesis image while passing to a finer definition, for example from 324 μm to 81 μm.

As a conclusion, the invention brings a high definition, large width, low irradiation dose, low emitting power, space-saving and low manufacturing costs imagery apparatus.

The invention claimed is:

1. X-ray or infrared imagery apparatus, for radiography or scanning, comprising:
   a support for receiving a body to be examined,
   an X-ray or light ray source provided with a focus for emitting a beam passing through a slit of a dose limiter driven in translation to sweep the body,
   a detector driven in translation to be irradiated or illuminated by the beam sweeping the body in order to detect an intensity attenuated along the X-ray or light ray propagation path through the body,
   an analog-to-digital converter to convert the detected intensities into data in order to determine an attenuation of the X-rays or light rays by the body, and
   a programmed computer to process the data resulting from the conversion of the detected intensities in order to obtain an image representing the attenuation of the X-rays or light rays,
   wherein the dose limiter is driven in translation with a speed proportional with the detector, controlled by the ratio of the distances between, on the one hand, the focus and the detector and, on the other hand, the focus and the dose limiter.

2. An X-ray or infrared imagery apparatus according to claim 1, wherein the X-ray or light ray beam is a secondary beam, resulting from a virtual focus formed by a primary beam emitted by an actual focus supplied by the source and reflected by a double reflection reflector laid out between the source and the dose limiter.

3. An X-ray or infrared imagery apparatus according to claim 2, wherein the dose limiter is laid out between the virtual focus and the body to be examined and displaced in translation in the same direction as the detector.

4. An X-ray or infrared imagery apparatus according to claim 2, wherein the dose limiter is laid out between the double reflection reflector and the virtual focus and displaced in the direction opposed to the detector.

5. An X-ray or infrared imagery apparatus according to claim 2 or 4, wherein the double reflection reflector comprises:
   an input reflector which extends along a first axial direction (E) and reflects the X-rays or light rays emitted by the actual focus parallel to said axial direction and,
   an output reflector which extends along a second axial direction (S) parallel but non-coaxial with the first axial direction, and
   wherein the X-rays or light rays reflected by the output reflector converge at the virtual focus on the second axial direction.

6. X-ray or infrared imagery apparatus, for radiography or scanning, comprising:
   a support for receiving a body to be examined,
   an X-ray or light ray source provided with a focus for emitting a beam passing through a slit of a dose limiter driven in translation to sweep the body,
   a detector driven in translation to be irradiated or illuminated by the beam sweeping the body in order to detect an intensity attenuated along the X-ray or light ray propagation path through the body,
   an analog-to-digital converter to convert the detected intensities into data in order to determine an attenuation of the X-rays or light rays by the body, and
   a programmed computer to process the data resulting from the conversion of the detected intensities in order to obtain an image representing the attenuation of the X-rays or light rays,
   wherein the dose limiter is driven in translation at the same speed than the detector, in front of a reflector which irradiates or illuminates the body to be examined with the rays emitted by the source and reflected in parallel webs.

7. An X-ray or infrared imagery apparatus according to claim 6, wherein the reflector comprises a collimator which collimates the non reflected rays towards the dose limiter slit when the dose limiter moves in front of the reflector.

8. An X-ray or infrared imagery apparatus according to claim 1, wherein the dose limiter comprises two plates moved one compared to the other by an adjustment means to adjust the slit width.

9. An X-ray or infrared imagery apparatus according to claim 8, wherein the two plates of the dose limiter are provided with a slit profile corresponding to a shift between two detection rods of the detector.

10. An X-ray or infrared imagery apparatus according to claim 1 or 6, wherein the dose limiter is driven in translation starting from a rest point for which the slit is outside the output section of a parallelepipedic box 4 which houses the source or outside the reflector output section to close the beam.

11. An X-ray or infrared imagery apparatus according to claim 1 or 6, wherein the dose limiter is driven at a speed identical or proportional to the detector speed $$\frac{U}{N\tau}$$

where U is the useful width of the detector irradiated or illuminated by the beam through the dose limiter slit, N is the number of lines of the detector, k is the number of photodiodes per line and $\tau$ is the photodiode charge transfer time of one line to the adjacent line, cumulatively from a first line $l_1$ to a last line $l_N$ of the detector, driven in opposite direction with respect to the charge transfer direction, that is to say in translation from the left to the right if the last line $l_N$ marks a left edge of the detector and the first line $l_1$, a right edge of the detector.

12. An X-ray or infrared imagery apparatus according to claim 11, wherein it comprises an interface between the analog-to-digital converter and the computer to transfer, at a frequency equal to the inverse charge transfer time $\tau^{-1}$, the data resulting from the conversion of the cumulated charges of every k photodiode of the last line $l_N$ of the detector.

13. An X-ray or infrared imagery apparatus according to claim 1 or 6, wherein the support is driven in rotation around the axis of rotation $\Omega$ and the computer is programmed to carry out the following steps:
   (1) to build a column generating vector and a line generating vector whose n and m terms respectively consist in data $c_i$ and $\rho_j$ resulting from the conversion of detected intensities at a same point $x_N$ of detector 9 during its translation and respectively for a first i and a second j angles of rotation, preferably orthogonal, of the support around the axis of rotation $\Omega$, said $c_i$ and $\rho_j$ data corresponding to a grid of n×m elementary areas of the body sectional plane which is perpendicular to the axis of rotation $\Omega$ and contains the considered point $x_N$ of detector 9,
   (2) to build an initial matrix (n, m) with the terms of the two generating vectors, by assigning to each elementary area a line and column term Bij which represents an attenuation coefficient and is equal to the half sum of the homologous term $c_i$ of the column generating vector divided by the number m of terms of the line generating vector and the homologous term $\rho_j$ of the line generating vector divided by number n of terms of the column generating vector, $$B_{ij} = \frac{1}{2}\left(\frac{\rho_j}{n} + \frac{c_i}{m}\right)$$

(3) to adjust the attenuation coefficient of each elementary area by using the following formula:

$$C_{ij} = \frac{\rho_j}{n} + \frac{c_i}{m} - \frac{1}{2nm}\left(\sum_{i=1}^{n} c_i + \sum_{j=1}^{m} \rho_j\right)$$

where, in this formula,
Cij=the desired value of the attenuation coefficient of the elementary area (i, j) of the grid
Bij=the initially estimated value
(n)=the line number of the initial matrix
(m)=the column number of the initial matrix
$\rho_j$ is term j of the line generating vector
$c_i$ is term i of the column generating vector
to obtain an image of the body sectional plane for the first and second angles of rotation, corresponding to an adjusted matrix for which the line and column border values calculated using the adjusted values (Cij) are respectively equal, for every line and every column, to the terms of the line and column generating vectors:

$\Sigma_{j=1}^{m} Cij = c_i$ $\Sigma_{i=1}^{n} Cij = \rho_j$ (4) to repeat steps (1) to (3) with data acquired for different pairs of rotation angles to respectively obtain different adjusted matrixes corresponding to different images of the body sectional plane for the different pairs of angles of rotation,
(5) to use a rotation operator to superimpose all the adjusted matrixes on a same pair of angles of rotation, and
(6) to display on the screen of the computer a synthesis image of the body sectional plane corresponding to a synthesis matrix of the attenuation coefficients of every elementary areas (i, j) of the grid, obtained by a term to term average of all the adjusted and superimposed matrixes.

14. An X-ray or infrared imagery apparatus according to claim 1 or 6, further comprising a mark fixed with respect to the detector and laid out outside a projection of the body on the detector or comprising a wire fixed with respect to the detector and aligned with the source and the axis of rotation $\Omega$.

15. An X-ray or infrared imagery apparatus according to claim 6, wherein the dose limiter comprises two plates moved one compared to the other by an adjustment means to adjust the slit width.

16. An X-ray or infrared imagery apparatus according to claim 15, wherein the two plates of the dose limiter are provided with a slit profile corresponding to a shift between two detection rods of the detector.

17. A non-transitory computer-readable medium encoded with the following stages of a computer program:
(1) to build a column generating vector and a line generating vector whose n and m terms respectively consist in data $c_i$ and $\rho_j$ corresponding to a grid of n×m elementary areas of a body sectional plane,
(2) to build an initial matrix (n, m) with the terms of the two generating vectors, by assigning to each elementary area a line and column term Bij which represents an attenuation coefficient and is equal to the half sum of the homologous term $c_i$ of the column generating vector divided by the number m of terms of the line generating vector and the homologous term $\rho_j$ of the line generating vector divided by number n of terms of the column generating vector, $$B_{ij} = \frac{1}{2}\left(\frac{\rho_j}{n} + \frac{c_i}{m}\right)$$

(3) to adjust the attenuation coefficient of each elementary area by using the following formula:

$$C_{ij} = \frac{\rho_j}{n} + \frac{c_i}{m} - \frac{1}{2nm}\left(\sum_{i=1}^{n} c_i + \sum_{j=1}^{m} \rho_j\right)$$

where, in this formula,
Cij=the desired value of the attenuation coefficient of the elementary area (i, j) of the grid
Bij=the initially estimated value
(n)=the line number of the initial matrix
(m)=the column number of the initial matrix
$\rho_j$ is term j of the line generating vector
$c_i$ is term i of the column generating vector
to obtain an image of the body sectional plane, corresponding to an adjusted matrix for which the line and column border values calculated using the adjusted values (Cij) are respectively equal, for every line and every column, to the terms of the line and column generating vectors:

$\Sigma_{j=1}^{m} Cij = c_i$ $\Sigma_{i=1}^{n} Cij = \rho_j$ (4) to repeat steps (1) to (3) with different data sets to respectively obtain different adjusted matrixes corresponding to different images of the body sectional plane,
(5) by means of a rotation operator, to superimpose all the adjusted matrixes on a same data set, and
(6) to display on the screen of the computer a synthesis image of the body sectional plane corresponding to a synthesis matrix of the attenuation coefficients of every elementary area (i, j) of the grid, obtained by a term to term average of all the adjusted and superimposed matrixes.

* * * * *